United States Patent [19]
McGary et al.

[11] Patent Number: 5,921,961
[45] Date of Patent: Jul. 13, 1999

[54] NON-REUSABLE RETRACTABLE SAFETY SYRINGE

[76] Inventors: R. Kern McGary, 5802 #B Cougar Dr., Austin, Tex. 78745-3814; S. William Jentzen, 3000 Artesian Dr., Cedar Creek, Tex. 78612

[21] Appl. No.: 09/005,905

[22] Filed: Jan. 12, 1998

Related U.S. Application Data

[62] Division of application No. 08/713,526, Sep. 13, 1996, Pat. No. 5,769,822.

[51] Int. Cl.$^6$ ................................................ A61M 5/00
[52] U.S. Cl. ......................... 604/110; 604/195; 604/218
[58] Field of Search ................................ 604/110, 195, 604/198, 187, 218, 228

[56] References Cited

U.S. PATENT DOCUMENTS 4,863,427  9/1989  Cocchi ................................ 604/110
5,226,881  7/1993  Pickhard ................................ 604/110
5,613,952  3/1997  Pressly, Sr. et al. ................ 604/195 X

*Primary Examiner*—John D. Yasko
*Attorney, Agent, or Firm*—Beirne Maynard & Parsons, L.L.P.

[57] ABSTRACT

A non-reusable retractable safety syringe is provided which has a hollow plunger and a seal member carried thereon. The provision of the plunger and the seal relative to the barrel permits the plunger, with sufficient strength, to carry applied pressure through the device during injection of a medicinal or other fluid into a patient, and yet permit the seal disposed at one end of the plunger to have maximum sealing integrity between the plunger and a cylindrical barrel disposed around the exterior of the plunger, to abate leakage of the liquid in a chamber within the barrel, as the plunger is manipulated from an expanded position to an expended position and thereafter to a third, or collapsed position. Designs for securing the seal relative to the plunger are disclosed. The syringe may be used to insert and/or withdraw fluid relative to the patient.

2 Claims, 6 Drawing Sheets

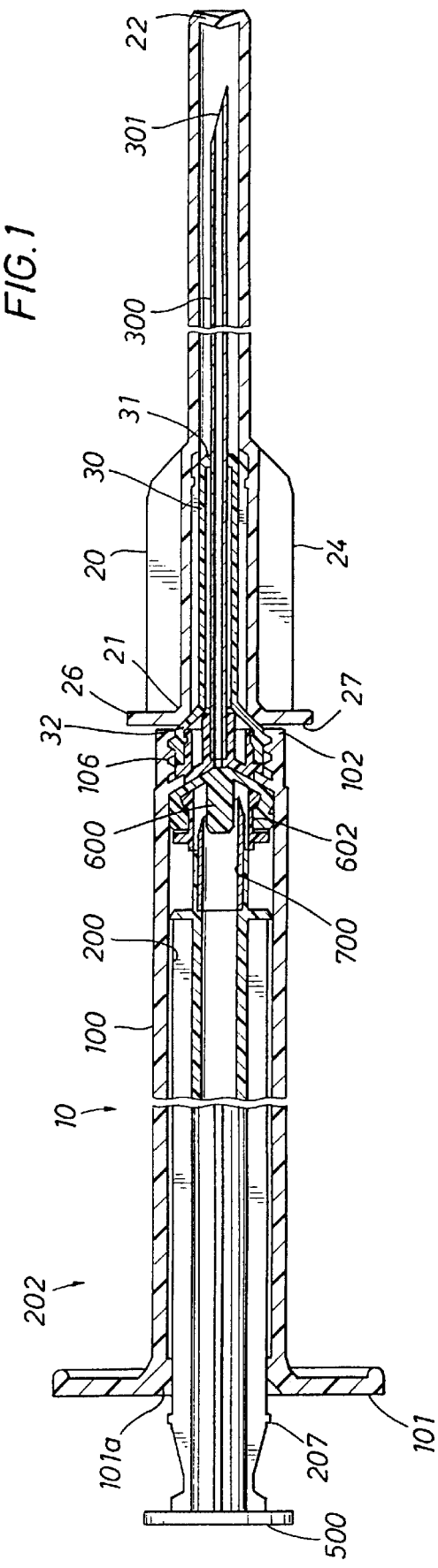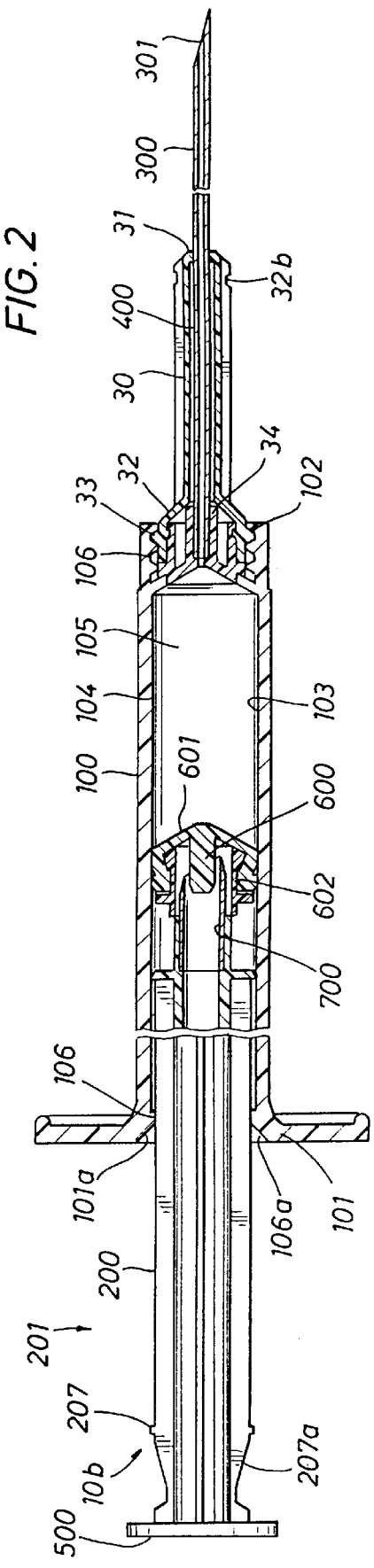

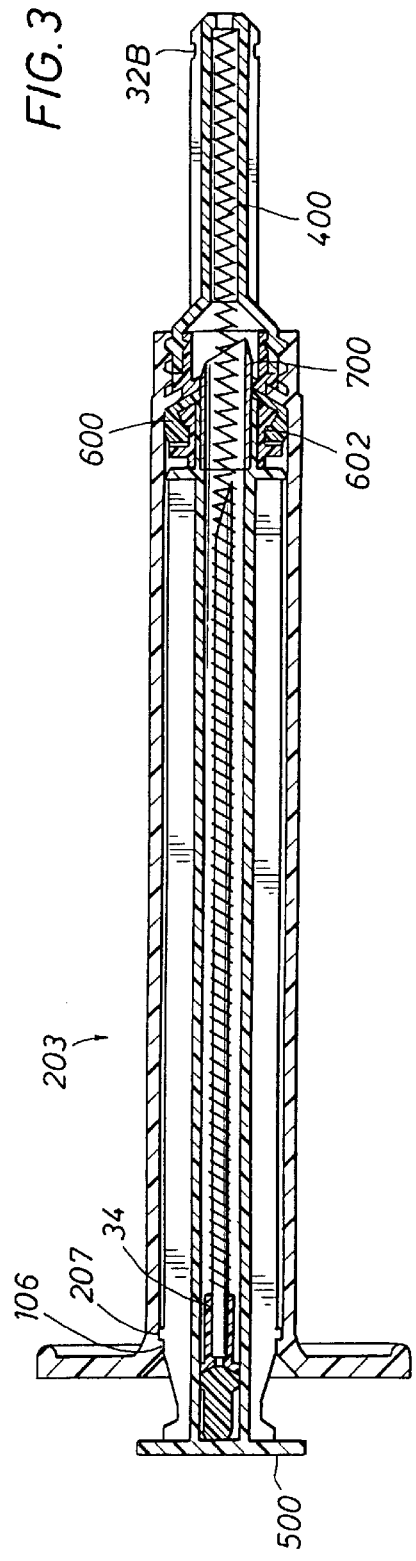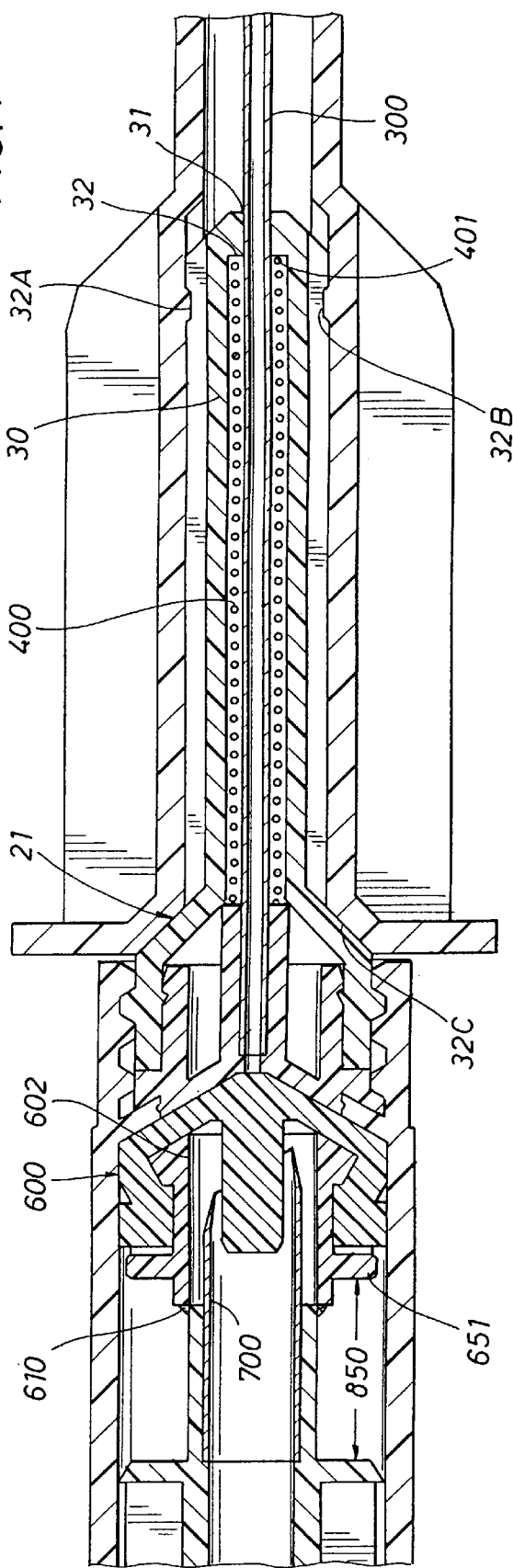

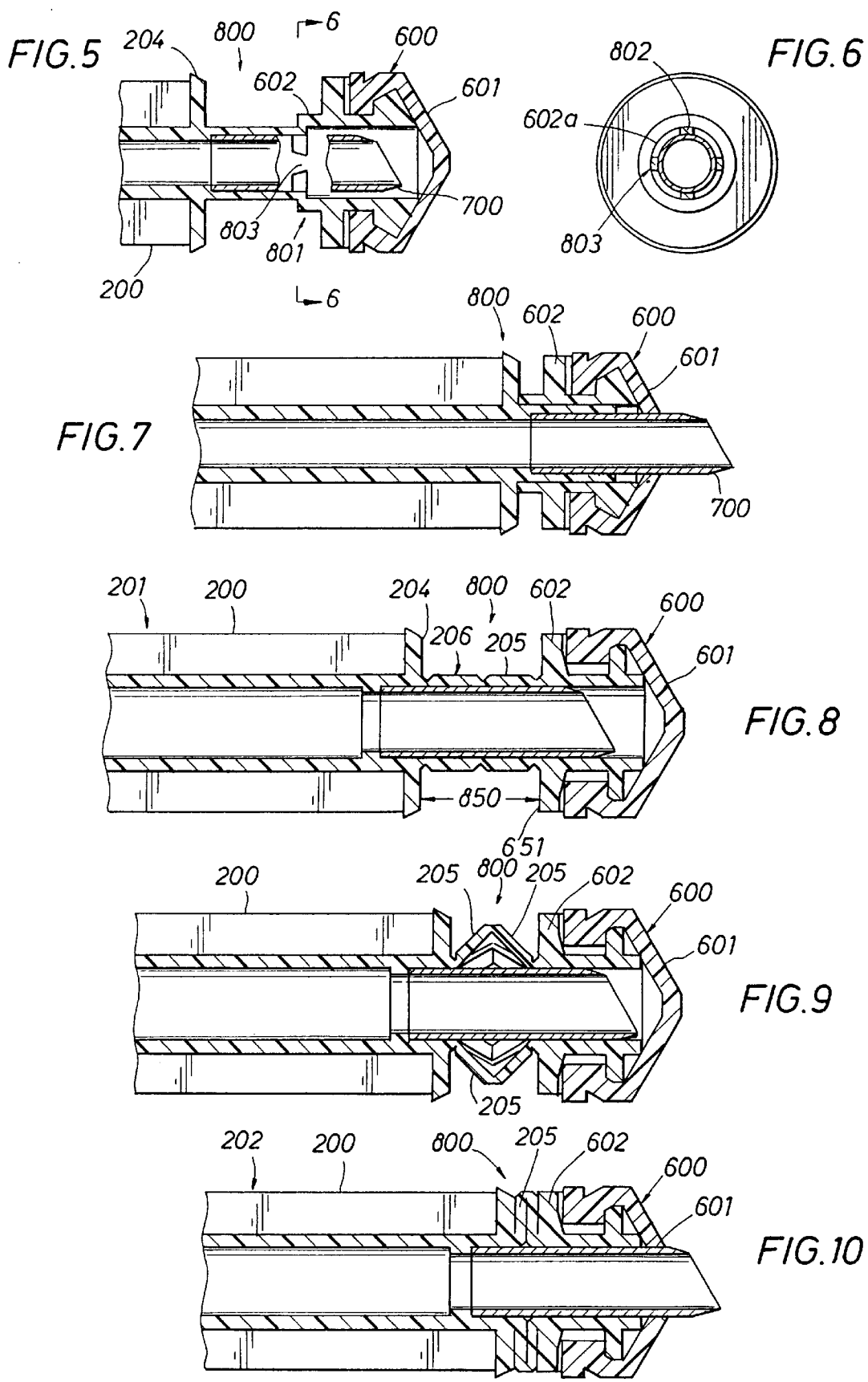

NON-REUSABLE RETRACTABLE SAFETY SYRINGE

CROSS-REFERENCE TO RELATED APPLICATION

This application is a divisional application of U.S. Ser. No. 08/713,526 filed on Sep. 13, 1996 now U.S. Pat. No. 5,769,822 and entitled "Non-Reusable Retractable Safety Syringe".

BACKGROUND OF THE INVENTION (1) Field of the Invention

This invention relates to a syringe device and, more particularly, to a non-reusable retractable syringe having an automatically retracting hypodermic needle to prevent reuse of the syringe. A method for delivering fluid to a patient and retracting the needle within the syringe after the fluid is delivered is disclosed.

(2) Description of Problems and the Prior Art

Many communicable diseases are commonly spread by contacting bodily and/or medicinal fluids of an infected person, reuse of hypodermic syringes is one of the most common causes of such contact.

Various mechanisms are provided in medical facilities for the disposal or destruction of syringes and hypodermic needles after usage. However, it is not uncommon for a medical worker to be scratched or punctured by a needle after usage and before disposal, resulting in injury and exposure to disease. Accordingly, there exists a need to protect personnel from accidental skin injuries from such contaminated needles, as well as the need to provide a safe and efficient means for disposing of the needles themselves.

There has been increased emphasis in designing hypodermic syringes with extendible shields which protect and project over the needle area after injections are completed. Such devices often involve manual manipulation of the shield over the needle after the injection is completed. It follows that when the shield is manually extended over the needle, the operator's hands or fingers may come into contact with the tip of the needle, thus causing risk of infection. To correct this problem, many devices have built-in biasing means which provide a shield over the needle after the injection is completed.

In U.S. Pat. No. 5,053,010, entitled "Safety Syringe with Retractable Needle", issued Oct. 1, 1991, there is shown and disclosed an improved safety syringe with retractable needle which allows retraction of the needle into a hollow plunger by additional forward pressure on the plunger after fluid is driven from the syringe into the patient. The syringe includes a hollow plunger which is inserted into one end of a cylindrical barrel and a hollow needle attached to the other end of the barrel. Biasing means are attached to the barrel for biasing the needle towards the hollow plunger, and means are provided for releasing the needle into the hollow plunger by applying additional forward pressure upon the plunger after the plunger is telescopically contracted relative to the barrel. This design, as well as others which are commercially available, provide a plunger which is made of a plastic material, such as polypropylene, which is manufactured by known techniques. Typically carried thereon is a sealing element which is made of a comparatively soft elastomeric material, which forms the seal between the housing and the moving plunger, to prevent leakage therebetween of the fluid to be injected.

The design disclosed in U.S. Pat. No. 5,053,010 incorporates a sliding elastomeric seal which displaces from its forward position to a retracted position, thereby allowing additional forward travel of the plunger to actuate the retraction mechanism. However, with this configuration, the soft nature of the seal depicted could allow it to slide prematurely during an injection. Increasing the stiffness of the sealing member would reduce the tendency to slide prematurely, but at the expense of the seal integrity.

There is need for an improved design of syringe in which an elastomer or other relatively soft seal can be used to provide maximum sealing integrity while also permitting sufficient pressure to be applied through the device to complete the injection, and thereafter to permit a cutter operatively associated with the plunger to continue to travel to cut the seal and, in turn, initiate retraction of the needle into the device after completion of the injection.

Moreover, it has been found desirable to prevent telescopic expansion of the plunger relative to the barrel of the device after activation of the retraction mechanism to assure that the needle tip cannot easily be re-exposed through withdrawal of the plunger.

SUMMARY OF THE INVENTION

The present invention provides a non-reusable retractable safety syringe. A cylindrical barrel is provided which has first and second barrel ends and an inside diameter wall there between. A chamber is provided for receipt of fluid within the barrel and between the first and second barrel end. A plastic hollow plunger is fully extendible into the barrel and is inserted into the first end of the barrel. The plunger is selectively movable from expanded position toward and placeable into an expended position. Thereafter, the plunger may be moved to a fully collapsed position relative to the second end of the barrel.

A hollow needle is secured relative to the second end of the barrel. Biasing means are provided in an initially secured relationship relative to the second end of the barrel for biasing the needle toward the hollow plunger. Means are provided for directing forward pressure upon the plunger, and sealing means include an elastomeric sealing member which is engaged to one end of the plunger for slidable sealing engagement with the inside diameter wall of the barrel. A cutting tip is provided and is carried by the plunger for cutting through the sealing member such that the biasing means releases the needle into the plunger when the plunger is at the fully collapsed position relative to the second end of the barrel.

The plunger may also include the sealing means which is engaged to one end of the plunger when the plunger is in the expanded and expended positions, as well as when the plunger is moving toward the collapsed position, with the sealing means being disengageable from one end of the plunger during movement of the plunger toward, but prior to, the plunger being placed at the collapsed position.

The syringe may comprise one of a number of engaging means for securing the plunger relative to the sealing means.

Fluid is drawn into the syringe through the needle. The needle is then implanted into the patient and the medication delivered via one-handed force applied to one end of the plunger—moving the plunger and sealing means to the expended position.

While or after removing the needle from the patient, additional one-hand force is applied to the plunger to move the plunger into the collapsed position. As the plunger collapses, the cutting tip extends through the sealing means and then through the needle retaining element to thereby release the biased needle into the plunger element of the device.

BRIEF DESCRIPTION OF THE DRAWINGS

FIG. 1 is a horizontal, sectional view of the device of the present invention prior to usage and, further, prior to introduction of medication therein.

FIG. 2 is a view similar to that of FIG. 1 showing the device with the plunger expanded and medication filling the interior portion of the chamber.

FIG. 3 is a view similar to those of FIGS. 1 and 2 showing the plunger collapsed within the barrel after medication has been injected into the patient, with the needle being retracted into the interior of the plunger, and the plunger being moved to the locked position.

FIG. 4 is a partial sectional view of a preferred means for securing the plunger relative to the sealing means.

FIG. 5 is a partial horizontal sectional view of the device in FIG. 1, illustrating an alternate preferred embodiment means for securing the sealing means to the plunger.

FIG. 6 is a cross-sectional view of the device of FIG. 5 taken along lines 6—6 of FIG. 5.

FIG. 7 is a view similar to FIG. 5 showing movement of the cutter through the sealing means.

FIG. 8 is a partial horizontal view of another preferred means of moving the plunger relative to the seal means, illustrating a series of support struts defined on the plunger in initial expanded position.

FIG. 9 is a view similar to that of FIG. 8 illustrating the operation and position of the support struts during movement of the plunger toward the collapsed position after reaching the expended position.

FIG. 10 is a view similar to that of FIGS. 8 and 9, illustrating the final collapsed position of the plunger resulting in the movement of the plunger and cutting of the seal element.

DESCRIPTION OF THE PREFERRED EMBODIMENTS

Figure 11:
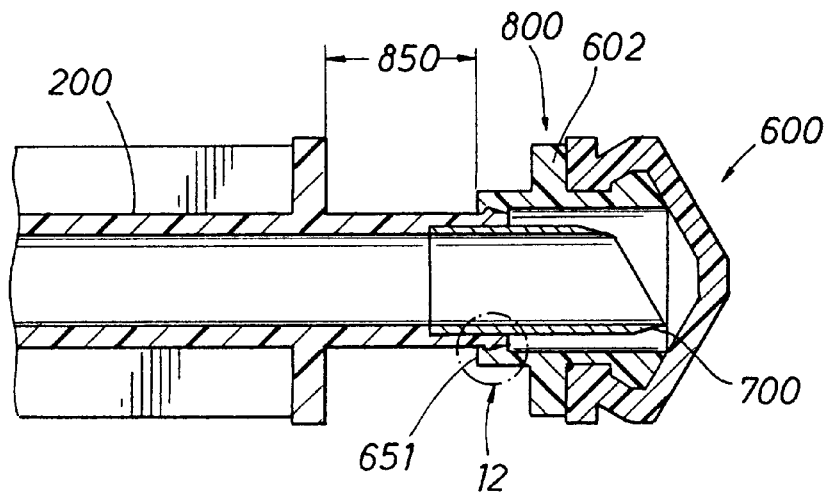
FIG. 11 is a horizontal sectional view of an alternate preferred embodiment of securing the plunger relative to the seal means.

Now, with first reference to FIG. 1, the syringe 10 of the present invention is shown with an outer elongated barrel element 100 interiorally receiving a plastic hollow plunger 200. The plastic hollow plunger is manufactured by known techniques for making such plastic components, but will be typically made through injection molding techniques of a plastic such as polypropylene.

Also, as shown in FIG. 1, the syringe device 10 of the present invention includes a hollow needle 300 having a pointed open end 301. An unextended portion of the needle 300 is securely engaged within a spring housing 30 with the needle 300 extending out of an open end 31 of the spring housing 30.

A cover 20 is slidably, but securely engaged around the spring housing 30 and has an inwardly circumferentially conically defined shoulder 21 which snugly engages a companion conically shaped shoulder 32C on the spring housing 30. As the cover 20 is moved toward the housing 100, it freely moves dorsally along the spring housing 30 until the portions 21 and 32C interface. Prior to interface, a circular groove 32B, which is indented around the exterior dorsal end of the spring housing 30, receives a companion abatement 32A around the interior diameter of the body 25 of the cover 20 to snap-secure the case 20 in place. This snap engagement may be overcome by hand manipulation of the guide 20 distally away from the housing 100.

The cover 20 has a closed end 22, extended radially around the exterior of the pointed open end 301 of the hollow needle 300. The cover, as shown, has a series of circumferentially extending wing member 23, 24 protruding outwardly from the body 25 of the cover 20 and formed as an integral unit or portion of body 25. additionally, the body 25 has a radially outwardly extending ring 26 including a shoulder 27 for assisting in one-handed removal of the cover 20. The human operator may remove the cover 20 by hand or finger application to either the ring 26 or one or more of the wings 23, 24, or both the ring 26 and one or more of the wings 23, 24 to unsnap the engagement 32A/32B.

Continuing with reference to FIGS. 1 and 2, there is shown an opening 101a in the barrel through which the plunger 200 is introduced through the first end 101 to the expended position 202. If medication or other fluid 105 is pre-introduced into the syringe 10 and into a chamber 104 within the inside diameter wall 103 of the barrel 100, it will be appreciated that the plunger 200 will be in the expanded position 201 as shown in FIG. 2. In other words, the syringe 10 is designed such that a medicinal fluid 105 may be placed into the syringe 10 and the cap or cover 20 snugly secured around a second or distal end 102 of the barrel or housing 101 and the cover 20 thereafter removed for injection of the fluid 105 into the patient.

Alternatively, the syringe 10 may be provided and positioned, such as in FIG. 1, the cover 20 thereafter removed at or about the application site and just before injection of the fluid 105 is needed. Thereafter, the cover 20 is removed and the pointed open end 301 of the needle 300 may be introduced into an exterior container for the fluid 105 and the plunger moved to the expanded position 201 (FIG. 2) to draw the fluid 105 through the pointed open end 301 into the chamber 104 by vacuum caused by the movement of the plunger 200 from the expended position 202 as shown in FIG. 1 to the expanded position 201, as shown in FIG. 2.

The barrel 100 has immediate its second or distal end 102 a series of radially and circumferentially extending thread-like elements 106 which are inter-engaged with companion thread-like elements 33 disposed around the exterior of the spring housing 30. Accordingly, the spring housing 30, during manufacture of the syringe 10, may be merely hand or mechanically threaded to the barrel 100 to secure the barrel 100 and the spring housing 30 together.

A spring lock device 34 is also initially contained within the spring housing 30, but is disengageable therefrom to the position shown in FIG. 3.

As stated above, the plunger 200 is manufactured of a plastic material which enables a considerable amount of force to be hand-applied to the plunger 200 through the finger or thumb of a human operator upon the means for directing forward pressure upon the plunger, such as ring or plate-like surface 500 (FIGS. 1, 2, and 3). This force is transmitted through the plunger 200 for movement of the fluid 105 through the pointed open end 301 of the needle 300 and introduction into the patient, thereby fully expending fluid within the chamber 104, and, thereafter, enabling a cutting tip 700 to further advance.

When the sealing means 600 has been fully cut and the spring lock 34 has been disengageably secured in relationship with the spring housing 30 and the barrel 100, the plunger 200 is moved to the collapsed position shown in FIG. 3. This technique is described in somewhat more detail in U.S. Pat. No. 5,053,010 entitled "Safety Syringe With Retractable Needle" issued Oct. 1, 1991.

Also, as stated above, it has been found that the sealing means 600 does not provide as effective sealing between the exterior thereof and the inside diameter wall 103 of the barrel 100 if the sealing means 600 includes a sealing member 601 (as in FIGS. 5–19) which is made of a material having the same given hardness as that of the plastic hollow plunger 200. A softer and more elastomeric material can be utilized to provide such an effective sealing means 600.

To assure that the barrel 100 and the plunger 200 do not telescopically expand relative to one another after the syringe 10 has been moved from the position as shown in FIG. 2 to the position as shown in FIG. 3, and, further, to avoid the possible loss of the needle 300 and/or exposure of the pointed open end 301 resulting in inadvertent contact with the patient or other human, the syringe 10 is provided with a radially interiorally extending lock ring 106 (FIG. 2) or other locking means, such as a series of inwardly projecting fingers, extensions, or the like, which are emplaced and defined on the barrel 100 immediate the first or dorsal end 101 thereof. Cooperative locking doughnut, or tabs, 207 are placed radially around the exterior of the plunger 200 just below or away from the plate or surface 500.

As the syringe 10 is moved from the position as shown in FIG. 2 to the collapsed position 203 shown in FIG. 3, the locking tabs or ring will be placed into contact with a beveled lock ring surface 106a (FIG. 2), and when such contact is made between surface 106a of the ring 106 and tabs 207, slight resistance to further telescopically retracting movements between the barrel 100 and the plunger 200 will be felt by the human operator through his/her finger upon plate 500. Continued application of slightly increased pressure on plate 500 will cause the locking tabs 207 to slide over and below the lock ring 106, with the lock ring 106 expanding, just slightly, immediate to the first end of 101. When the locking tabs 207 pass inwardly below the lock ring 106, the lock ring 106 will flexibly move back into its initial position and, in fact, will radially inwardly retract, just slightly, due to contact upon a profile surface 207a defined on the plunger 200. Since the lock ring 106 now has its outer surface in contact with the surface 207a of the plunger 200, the barrel 100 and the plunger 200 are inter-engageably locked by the position of the lock ring 106 relative to outwardly extending locking tabs 207.

As shown in FIG. 4, the plunger 200 is positioned to the fully expended position 202 and the distal end of the plunger 204 is about to move to the collapsed position, allowing the cutter 700 to continue through the sealing means 600. This permits the spring lock 34 to become disengaged such that the biasing or spring means 400 now may be released, causing the force contained within the spring 400 when it is in its retracted position as shown in FIG. 1, to urge the spring lock 34 away from the spring lock housing 35. The spring 400 has an end 401 which is snuggly contained within the spring housing 30 by means of an arresting shoulder 32 which extends internally, with an open end 31 permitting the hollow needle 300 to extend thereout.

Now with reference to FIGS. 5 through 19, there are shown a number of alternate preferred means 800 for engaging the plunger 200 to the sealing means 600. For example, with first reference to FIGS. 5, 6 and 7, there is shown an engaging means 800 which is provided on the distal end of plunger 204. As shown, the engaging means 800 is defined by a series of radially extending support struts 802 which are members extending between the plunger 200 and the sealing means 600. The struts 802 can be made of the same material utilized to make the plunger 200 and/or the housing 602 for the sealing member 601. Each of the support struts 802 will have an external diameter 803 which is slightly less than the internal diameter 602a of the companion housing 602 of the sealing means 600. As pressure is applied to the plunger 600, the support struts 802 will be caused to be sheared, thus permitting the plunger 200 to provide means 801 for telescopically engaging the plunger 200 to the distal end 204 relative to the sealing means 600, and the plunger 200 will continue to move interiorally of the sealing means 600 to the collapsed position shown in FIG. 7. The number and size of the struts can be varied to achieve different levels of shear forces required to collapse the sealing means. For example, as shown in FIG. 4, this may be simply a very thin connecting ring. 610 of plastic material between the housing 602 and the end of the plunger 200.

Now referring to FIGS. 8, 9, 10, another alternative means for securing the end of the plunger 200 to the sealing means 600 is shown. With first reference to FIG. 8, the device is shown in expended position 201, with the distal end 204 of the plunger 200 providing either one or a series of vertically collapsible support pleats 206 having a series of vertically positioned horizontal pleat elements 205. As pressure is applied to the plate 500 of the plunger 200, the plunger will telescope relative to the barrel 100 and the pleats 206 will first be caused not to be able to sustain resistance to such amount of pressure and will, in turn, cause the collapsible pleat 205 members to collapse as the pleats 206 are flexed, as shown in FIG. 9, to the collapsed position 202 as shown in FIG. 10.

Of course, the horizontal pleats 206 can sustain the amount of pressure necessary to cause the plunger 200 to telescope retractedly relative to the barrel 100 to eject the medication or fluid 105 from the chamber 104 and, thus, close the chamber 104, i.e., the expended position, without deflecting the collapsible members 205. When all medication is ejected through the pointed open end 301 of the needle, and when the seal means 600 is moved to the abutting position as shown in FIG. 1, the resistance to further movement caused thereby will result in the struts 205 moving from the position as shown in FIG. 8 to the position as shown in 9 as increased pressure is applied to the plate 500 and transmitted through the plunger 200. This increased mechanical pressure will move the plunger 200 to the collapsed position 202 as shown in FIG. 10 when the plunger 200 has moved relative to the barrel 100 to cut through the seal means 600.

Figure 12:
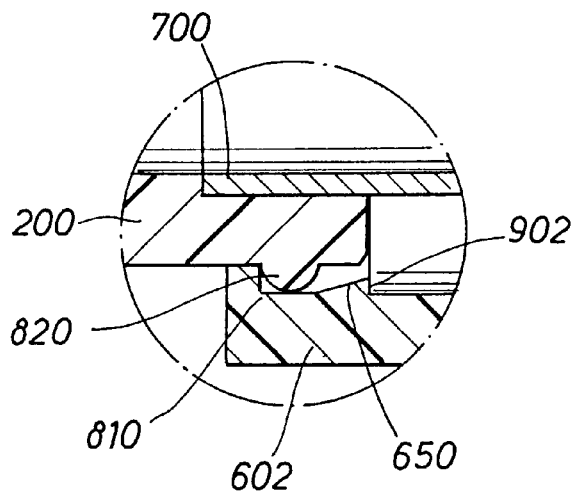
FIG. 12 is a detailed horizontal sectional view of the area highlighted in FIG. 11.

Now with respect to FIGS. 11 and 12, there is shown still another alternate preferred means 800 for engaging the plunger 200 to the sealing means 600 which uses a snap-fitting detent assembly comprising a ring 820 and a ring recess 810. As shown in the blow-up FIG. 12, the plunger 200 is secured to the housing element 602 of the seal means 600 by means of a ring 820 received within a beveled shoulder 650 of the seal means 600. The bevel-shaped shoulder 650 snugly secures the ring 820 for affixation purposes. However, when sufficient pressure is applied through the plunger 200, the ring 820 will move along the shoulder 650 such that the ring 820 is caused to be flexed inwardly just slightly until it reaches the profile 902 carried on the member 602, at which time the ring 820 will be caused to radially expand, just slightly, into snug securing engagement relative to the profile 902 and thus permits continued movement of the plunger 200 from the expended position to the collapsed position to be accomplished.

Housing 602 is molded as a separate component and snapped onto the end of plunger 200. The distal end of plunger 200 has the annular ring 820 molded onto it. The interior of the housing 602 has a mating recess 810 whose shoulder 650 resists expansion and compression. However, the shoulder 650 resists compression of the ring component 820 and allows it to be overcome with a predetermined amount of force, thereby allowing the cutter 700 to advance.

Figure 13:
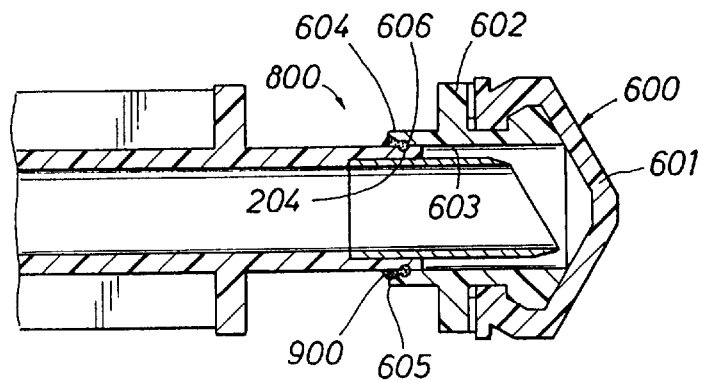
FIG. 13 is a view similar to that shown in FIG. 11 showing yet another alternative preferred means for securing the plunger relative to the seal means.

Now with respect to FIG. 13, there is shown still another alternate preferred means 800 for engaging the plunger 200 to the sealing means 600, using either one or a series of adhesive spots 606. When the plunger reaches the expended position, hand pressure for continued forward movement of the plunger 200 will be resisted and further applied pressure will shear or break the spots 606 so that the plunger may thereafter move to the collapsed position. There are, of course, a number of adhesives which can be utilized, such as cyanoacrylate, Super-Glue™, Durabond™ or UV-15™, made by Masterbond.

Also, as shown in FIG. 13, the housing 602 has an internal diameter 603 which, at the dorsal end 605, is contourly beveled to provide a smooth radially and outwardly extending shoulder 606 for application of the adhesive and also to the outer surface of the plunger distal end 204. The distal end 204 of the plunger is first flexed somewhat inwardly to permit the shoulder configuration of the dorsal end 605 to come over, just slightly, the end 204, such that, in some circumstances, the use of the adhesive means 900 may be combined with slight mechanical inward bias between the sealing member housing 602 and the end 204 such that the sealing means 600 and the plunger 200 are engaged together by a combination of mechanical and chemical means. The amount of adhesive used, the extent to which it completely surrounds the housing 602, and the shape of the bead provided through application of the adhesive, all act to effect the amount of force required to move the plunger 200 relative to the sealing means 600. of course, as the adhesive engagement between the members is broken, the plunger 204 will continue inwardly within the housing 602 to effect operation of the device 10, as shown in FIGS. 1, 2, and 3.

Figure 14:
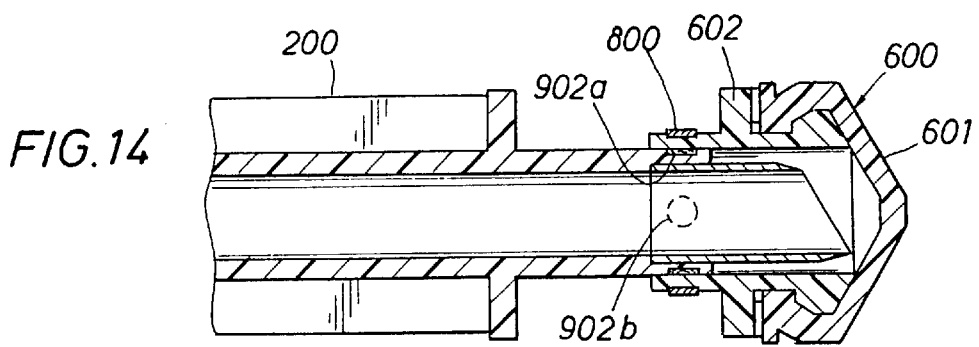
FIG. 14 is a horizontal sectional view of still another alternative preferred embodiment for securing the plunger to the sealing means.

Now with respect to FIG. 14, there is shown yet another alternative embodiment, somewhat similar to FIG. 13. FIG. 14 shows housing 602 firmly attached to the distal end of plunger 200 by means of ultrasonic, heat staking, friction welding or any other means resulting in a similar weld, as is well known to those skilled in such arts. Each of these techniques can be used to create one or more rigid connections 902a and 902b between parts 602 and 200.

Figure 15:
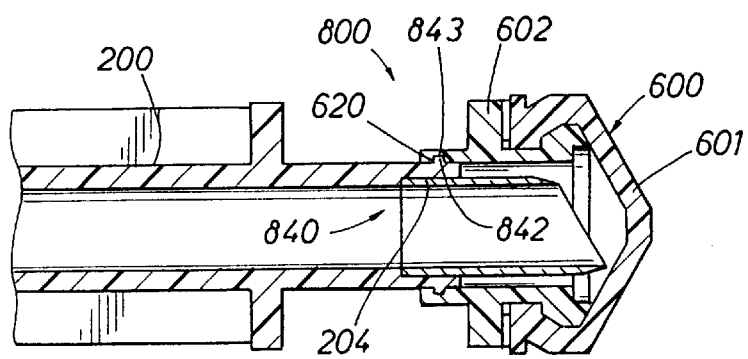
FIG. 15 is a view of still another alternative preferred embodiment shown in the initial expanded position.
Figure 16:
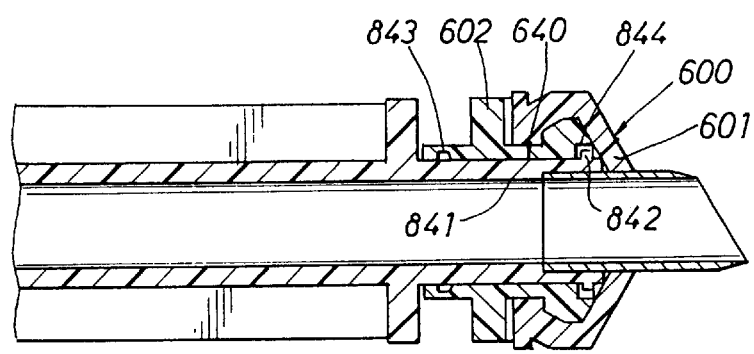
FIG. 16 is a horizontal section view of the device depicted in FIG. 15, illustrating the sealing means in the fully collapsed position.

With respect to FIG. 15 and 16, another alternative preferred means 800 for engaging the plunger 200 to the sealing means 600 is shown. As shown in FIG. 15, a projection 842 which may be continuous or collet-like outwardly extends from the tip of the end of the plunger 200 and into the sealing means 600 at receptacle 843. The shape of this projection resists pulling out of the sealing means 600. Further, under forward pressure the shape tends to expand the sealing means tighter against the barrel 100 to prevent leakage. Under sufficient pressure, however, the projection 842 can no longer resist movement of the sealing means 600, allowing it to collapse to the position shown in FIG. 16 and the profile 844 now receives the projection(s) 842 which are flexed outwardly after passage across the internal housing wall 640. It will be appreciated that a shoulder 620 is provided on the housing 602 and is substantially vertical (in the views of FIGS. 15 and 16) to the horizontally disposed plunger 200. this assists in enabling the plunger 200, securing means 800 and the sending means 600 to travel as a unit from the position shown in FIG. 1 to that shown in FIG. 2, during introduction of fluid 105.

Figure 17:
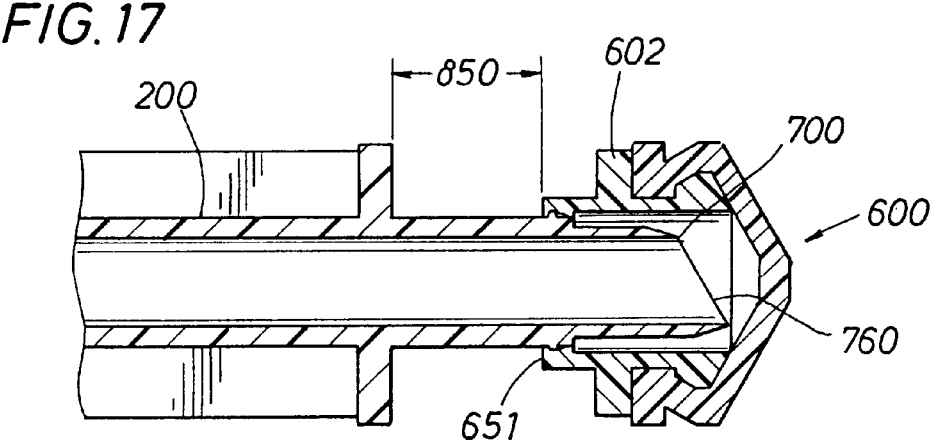
FIG. 17 is another illustration of still another preferred embodiment, showing the cutter element being defined at the distal end of the plunger.

Now, with reference to FIG. 17, yet another embodiment of the invention is illustrated in which the cutter 700 is an integral component of the plunger 200 and, in fact, is formed near the distal end of the plunger member 200.

The distance 850 defines the travel of the plunger 200 to the no-go end 651 of the housing 602 of the seal means 600. Travel of the plunger 200 this distance 850 is the distance from the expended position to the collapsed position in all embodiments shown in the FIGS.

Figure 18:
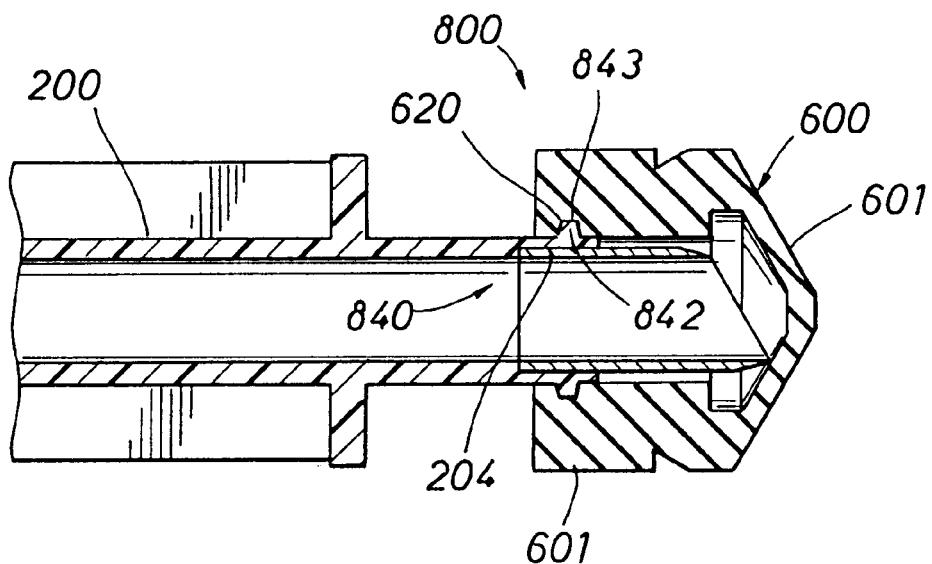
FIG. 18 is a view similar to that of FIG. 15, but showing yet another alternative embodiment of providing the sealing means 600 in a single element, thereby eliminating the need for the housing member 602.
Figure 19:
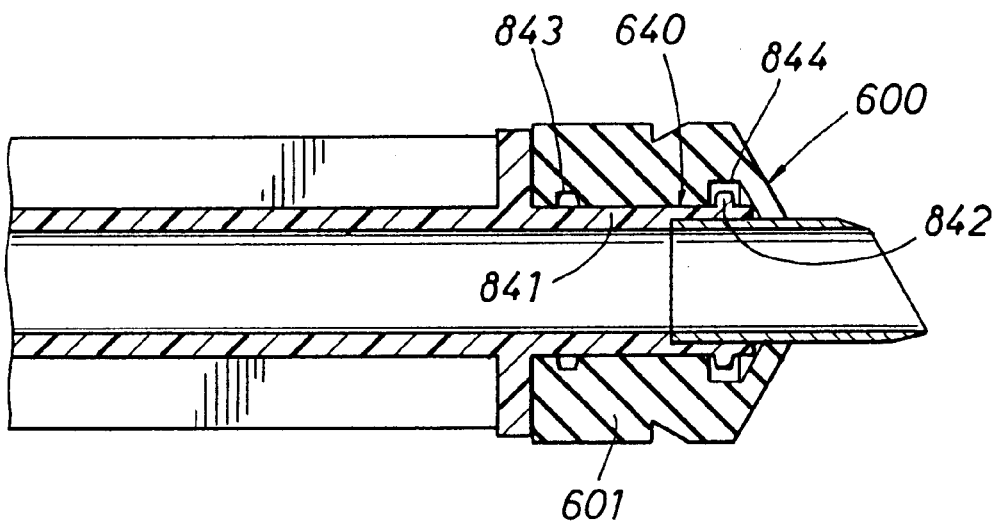
FIG. 19 is a view similar to that of FIG. 18 but showing the embodiment of FIG. 18 moved to the collapsed position.

FIGS. 18 and 19 show yet another embodiment of the invention where the sealing means 600 is provided with the seal 601 extended and used without a separate housing 602. The seal element 601 still provides the groove 843 with the shoulder 620 for receipt of the protrusion 842. Some economical savings might be enjoyed if it is desired to use the construction as shown in FIGS. 18 and 19.

The invention also contemplates usage of a needle 700 with the cutting end as contoured such as 760 (FIG. 17). Alternatively, the cutting configuration 760 may provide that the end of the cutter 700 is dome-like or pyramid-like or any other variant to the form 760.

The invention includes the method of delivering fluid to a patient utilizing the device 10 of the present invention. When in the "ready" or expanded position of FIG. 2, after removal of the cover means 20 (FIG. 1), the method contemplates the use of the apparatus 10 which will include inter-engagement of the plunger 200 relative to the seal means 600 in one of the preferred embodiments. The needle is implanted into the patient by the operator either by application of hand or fingers around the exterior of the barrel 100 and/or application of forward pressure to the plate 500 by the operator. Force is applied one handedly to one end of the plunger 200 to coerce the fluid 105 from within the chamber 104 within the barrel 100 and into the patient through an arm, leg, or otherwise.

The plunger is moved to the expended position shown in FIG. 2 and, thereafter, additional one handed force is applied to the plate or surface 500 at one end of the plunger 200 to further drive the plunger to the collapsed position (FIG. 3) so that the cutting tip 700 extends through the spring lock housing 30 to thereby release the biased needle 300 into the plunger 200. The plunger 200 then is locked relative to the barrel 100 by the inter-engagement of the locking tabs 207 relative to the lock ring 106 (FIG. 3).

Although the invention has been described in terms of specified embodiments which are set forth in detail, it should be understood that it is by illustration only and that the invention is not necessarily limited thereto, since other alternative embodiments and operating techniques will become apparent to those skilled in the art in view of the disclosure. Accordingly, modifications are contemplated which can be made without departing from the spirit of the described invention.

What is claimed and desired to be secured by Letters Patent is:

1. A non-reusable retractable safety syringe comprising:
   (a) a cylindrical barrel having first and second barrel ends and an inside diameter wall there between;
   (b) a chamber for receipt of fluid within said barrel and between said first and second barrel ends;
   (c) a plastic hollow plunger having a distal end, said plunger being extendable into said barrel through the first end of said barrel, and selectively movable from expanded position toward an expended position;
   (d) means for permitting the plunger to thereafter move to a collapsed position relative to the second end of the barrel;
   (e) a hollow needle in secured relationship relative to the second end of the barrel;
   (f) biasing means in initially secured relationship relative to the second end of the barrel for biasing the needle toward the hollow plunger;
   (g) means for directing forward pressure upon said plunger;
   (h) sealing means including a tubular housing having a distal end and further including an elastomeric sealing member engaged to one end of the plunger for slidable sealing engagement with the inside diameter wall of the barrel;
   (i) a cutting tip carried by the plunger for cutting through the sealing member such that the biasing means thereafter releases the needle into the plunger when the plunger is at the collapsed position relative to the second end of the barrel; and
   (j) means for engaging the plunger to the sealing means, the engaging means including an inter-engaging and selectively disengagable snap-fitting detent assembly including a ring and a ring recess.

2. A non-reusable retractable safety syringe comprising:
   (a) a cylindrical barrel having first and second barrel ends and an inside diameter wall there between;
   (b) a chamber for receipt of fluid within said barrel and between said first and second barrel ends;
   (c) a plastic hollow plunger having a distal end, said plunger being extendable into said barrel through the first end of said barrel, and selectively movable from expanded position toward an expended position;
   (d) means for permitting the plunger to thereafter move to a collapsed position relative to the second end of the barrel;
   (e) a hollow needle in secured relationship relative to the second end of the barrel;
   (f) biasing means in initially secured relationship relative to the second end of the barrel for biasing the needle toward the hollow plunger;
   (g) means for directing forward pressure upon said plunger;
   (h) sealing means including an elastomeric sealing member and engaged to one end of the plunger for slidable sealing engagement with the inside diameter wall of the barrel;
   (i) a cutting tip carried by the plunger for cutting through the sealing member such that the biasing means thereafter releases the needle into the plunger when the plunger is at the collapsed position relative to the second end of the barrel; and
   (j) means for engaging the plunger to the sealing means comprising a locking assembly including a ring element defined on one of the plunger and the sealing means and a companion locking groove on the other of the plunger and the sealing means.

* * * * *